(12) United States Patent
Lanier

(10) Patent No.: US 6,871,651 B2
(45) Date of Patent: Mar. 29, 2005

(54) OPHTHALMIC SURGICAL DRAPE SUPPORT

(76) Inventor: Jeffrey Day Lanier, 8 Tiel Way, Houston, TX (US) 77019

( * ) Notice: Subject to any disclaimer, the term of this patent is extended or adjusted under 35 U.S.C. 154(b) by 47 days.

(21) Appl. No.: 10/616,805

(22) Filed: Jul. 10, 2003

(65) Prior Publication Data

US 2005/0005943 A1   Jan. 13, 2005

(51) Int. Cl.⁷ .............................................. A61B 19/08
(52) U.S. Cl. ..................... 128/852; 128/849; 128/858; 602/74
(58) Field of Search .............. 128/852, 849, 128/850, 851, 853, 854, 855, 856, 858, 898, 128/912, 200.24; 2/410, 424, 15, 9, 206; 602/74

(56) References Cited

U.S. PATENT DOCUMENTS

| | | | |
|---|---|---|---|
| 3,403,677 A * | 10/1968 | Struve | 128/200.24 |
| 4,122,848 A | 10/1978 | Carpel | |
| 4,223,669 A | 9/1980 | Morledge | |
| 4,465,066 A | 8/1984 | Carpel | |
| 4,699,131 A | 10/1987 | Crook et al. | |
| 4,739,753 A * | 4/1988 | Brehm | 128/200.24 |
| 4,869,271 A | 9/1989 | Idris | |
| 4,966,168 A | 10/1990 | Glassman | |
| 5,042,507 A | 8/1991 | Dowdy | |
| 5,127,423 A * | 7/1992 | Draeger | 128/849 |
| 5,140,997 A | 8/1992 | Glassman | |
| 5,213,114 A | 5/1993 | Bailey, Jr. | |
| 5,361,780 A * | 11/1994 | Kellan | 128/849 |
| 5,409,761 A | 4/1995 | Langley | |
| 5,464,025 A | 11/1995 | Charles et al. | |
| 5,546,961 A | 8/1996 | Harrison | |
| 5,620,010 A | 4/1997 | Vancaillie et al. | |
| 5,632,284 A | 5/1997 | Graether | |
| 5,709,220 A * | 1/1998 | Kellan | 128/849 |
| 5,709,221 A | 1/1998 | Vancaillie et al. | |
| 5,960,794 A | 10/1999 | Shaw | |
| 6,070,587 A | 6/2000 | Levitt et al. | |
| 6,105,579 A | 8/2000 | Levitt et al. | |
| 6,199,551 B1 | 3/2001 | Kuslich | |
| 6,213,124 B1 * | 4/2001 | Butterworth | 128/853 |
| 6,286,511 B1 * | 9/2001 | Levitt et al. | 128/849 |
| 6,345,621 B1 * | 2/2002 | Chandler et al. | 128/849 |
| 6,405,730 B2 * | 6/2002 | Levitt et al. | 128/849 |
| 6,675,805 B1 * | 1/2004 | Graether | 128/849 |

* cited by examiner

Primary Examiner—Fadi H. Dahbour
(74) Attorney, Agent, or Firm—Gary L. Bush; Andrews Kurth LLP

(57) ABSTRACT

An apparatus for supporting a surgical drape during eye surgery comprising a flexible supply tube and a flexible suction tube which is easily formed by hand to maintain a desired shape and which serves the dual role of supporting the surgical drape above the patient's nose and mouth and providing a breathing environment by supplying air or oxygen and by removing exhaled $CO_2$-rich air. Ports are located at the upper ends of the supply and suction tubes near the patient's face. The lower ends of the supply and suction tubes are equipped with optional valves and coupled to an oxygen source and a suction source, respectively. A bracket is disposed beneath the patient and supports the tubes near their lower ends.

15 Claims, 2 Drawing Sheets

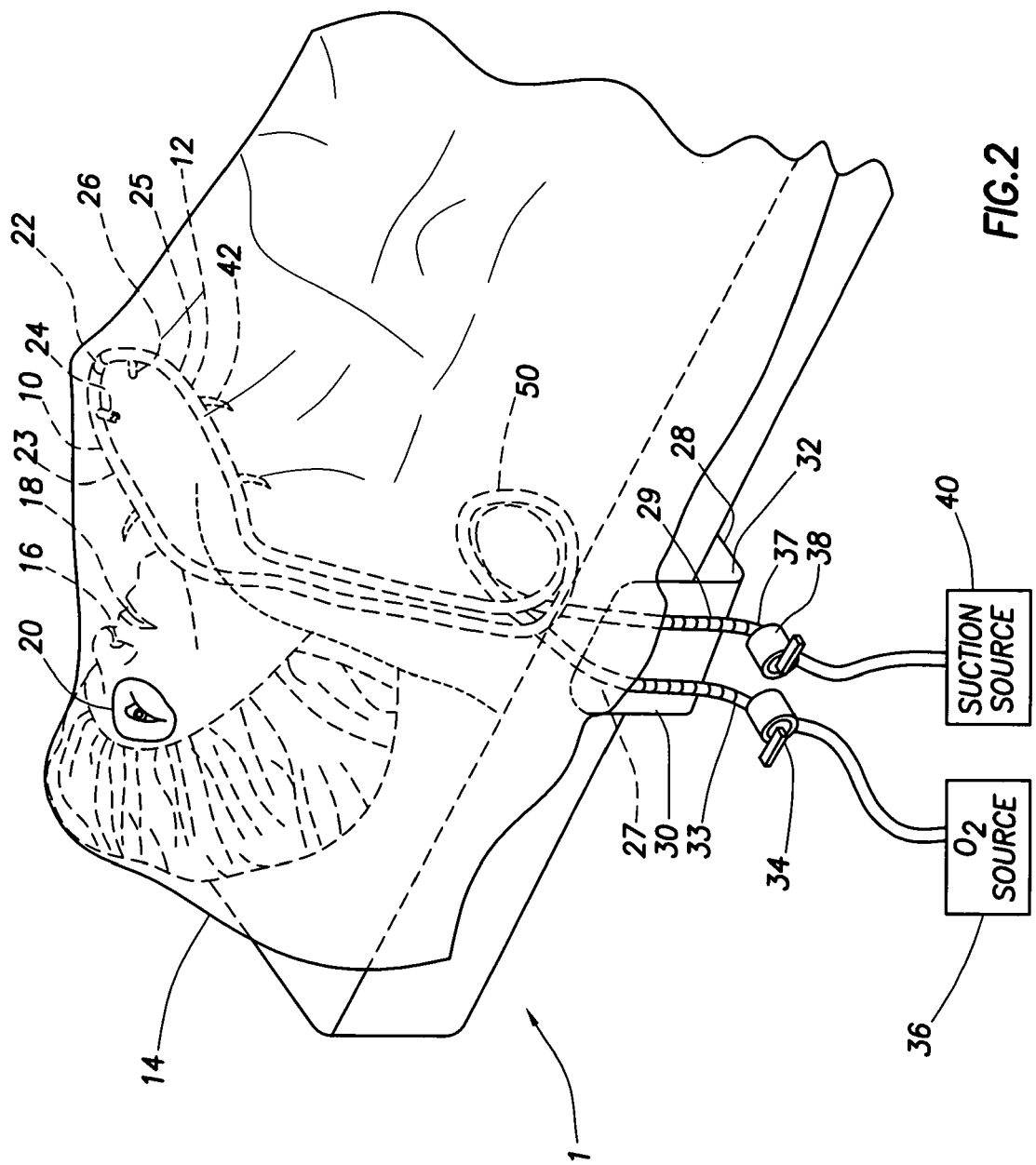

OPHTHALMIC SURGICAL DRAPE SUPPORT

BACKGROUND OF THE INVENTION

1. Field of the Invention

This invention relates generally to an ophthalmic surgical drape support and specifically to a drape support with a device to supply oxygen or air to and remove carbon dioxide from the patient.

2. Description of the Prior Art

For eye surgery, a local anesthetic is often used instead of general anesthesia. It is imperative that the patient remains motionless during the delicate surgical procedure to avoid unintentional damage to tissue. The patient, other than that portion of the body which is undergoing surgery, is covered by a drape to reduce the possibility of contamination. If the drape rests on the patient's face, it may cling to the nostrils and mouth during inhalation and hamper breathing. A patient who feels suffocated may thrash about to clear the drape.

One method to keep the drape clear of the nose and mouth is disclosed by Carpel in U.S. Pat. No. 4,465,066. Carpel teaches using a 'T'-shaped drape support which secures to each cheek and to the bridge of the nose with double-sided adhesive pads to keep the drape clear of the nose and mouth. However, a patient may suffer claustrophobia, anxiety or irritation by having the drape support in contact with the face.

Moreledge, in U.S. Pat. No. 4,223,669, addresses this problem with a drape support having a 'U'-shaped horizontal base which is placed beneath the patient's head, a vertical mast which rises above the patient's face, and a horizontal transverse member which extends from the top of the mast and passes above the patient's face to keep the drape clear of the nose and mouth. While this apparatus relieves some of the patient's apprehension, the air underneath the impermeable drape may become hot and stale due to exhalation which adds to the claustrophobic conditions of having a drape over the face. A cannula inserted into the nasal passageway to provide fresh oxygen to the patient, can be uncomfortable and result in irritation to the nasal passageway.

Crook (U.S. Pat. No. 4,699,131) discloses a surgical drape support which keeps the drape off of the patient's nose and mouth. Crook teaches to supply oxygen into the tent formed above the patient's face by an independent hose, thus obviating the need for the nasal cannula. Brehm (U.S. Pat. No. 4,739,753) refines the concept by integrating an oxygen supply into the drape support. The drape support has a rigid base bracket which is positioned beneath the patient and holds a flexible conduit which fulfills the dual role of supplying the patient with fresh air and holding the drape off of the patient's lower face. While both of these methods accommodate an air or oxygen supply, neither provides for drawing off the exhaled $CO_2$-rich air. The $CO_2$, which accumulates under the drape may give rise to acidosis and hypertension. Simply allowing the four sides of the drape to remain loose is not always effective in venting the $CO_2$.

Glassman (U.S. Pat. No. 5,140,997) reveals an ophthalmological surgical drape with integral breathing tubes for supplying oxygen to the patient at the nostrils and removing exhaled $CO_2$-rich air. Because the breathing means are one with the drape, the drape is fitted directly to the patient's face. Covering the patient's entire face with a drape may still lead to claustrophobia, anxiety, apprehension or irritation.

3. Identification of Objects of the Invention

A primary object of the invention is to provide an ophthalmological surgical drape support which keeps the surgical drape clear of the patient's nostrils and mouth during eye surgery.

Another object of the invention is to provide a source of oxygen or fresh air to the patient for breathing without the use of a cannula.

Another object of the invention is to provide for removal of exhaled $CO_2$-rich air from underneath the surgical drape.

Another object of the invention is to provide a drape support which is easily manipulated by hand to allow use with the myriad sizes and shapes of patients.

SUMMARY OF THE INVENTION

The objects identified above, as well as other features and advantages of the invention are incorporated in an apparatus for supporting a surgical drape during eye surgery comprising a flexible supply tube and a flexible suction tube which is easily formed by hand to maintain a desired shape and which serves the dual role of supporting the surgical drape above the patient's nose and mouth and providing a breathing environment by supplying oxygen and by removing exhaled $CO_2$-rich air. One or more supply ports are located at the upper end of the supply tube, and one or more suction ports are located at the upper end of the suction tube. The lower ends of the supply and suction tubes are equipped with valves and coupled to an oxygen source and a suction source, respectively. A bracket is disposed beneath the patient and supports the tubes near their lower ends.

BRIEF DESCRIPTION OF THE DRAWINGS

The invention is described in detail hereinafter on the basis of the embodiments represented schematically in the accompanying figure, in which:

FIG. 2 illustrates an alternate embodiment of the invention with a loop at or near the base.

DESCRIPTION OF THE PREFERRED EMBODIMENT OF THE INVENTION

Figure 1:
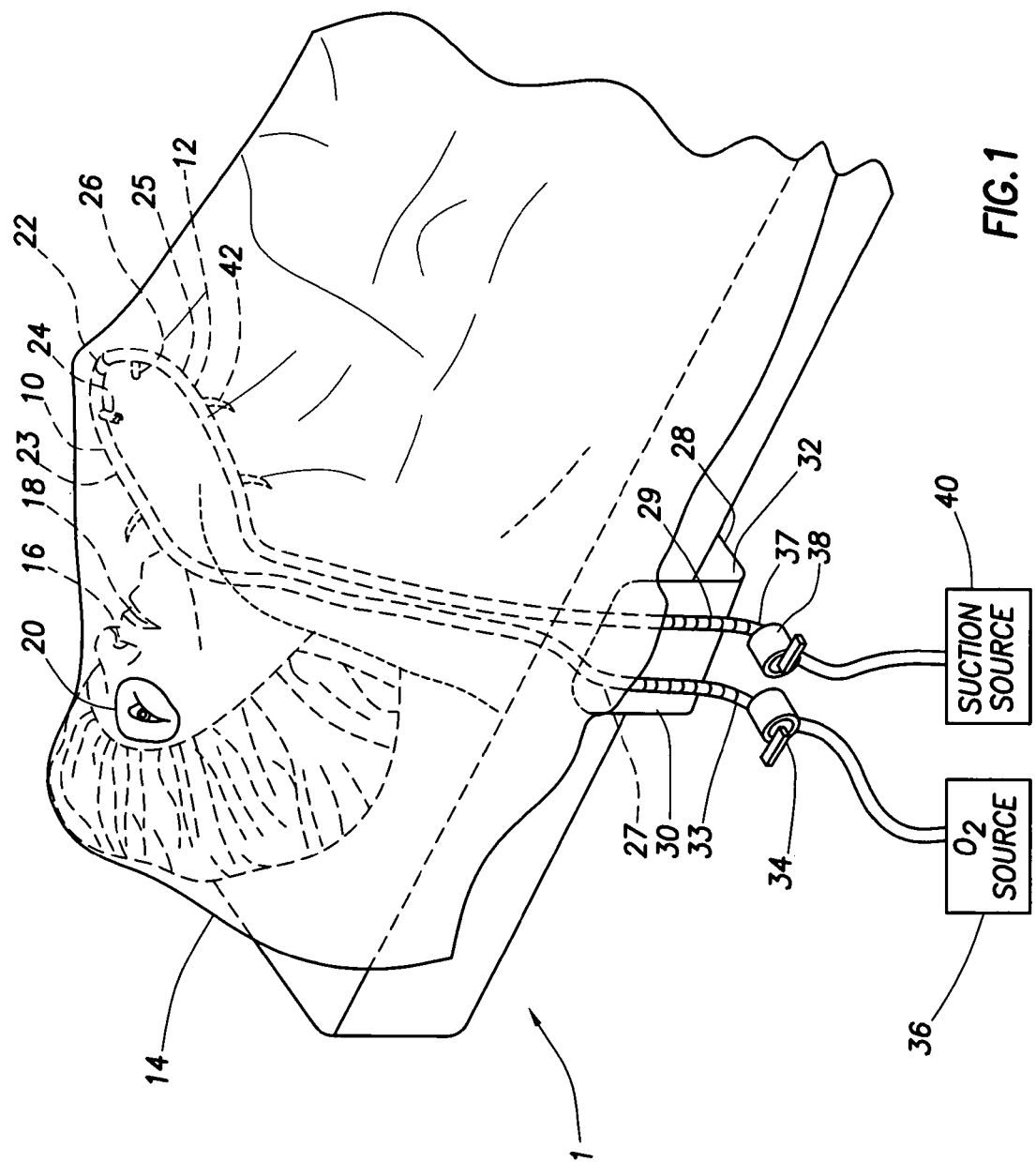
FIG. 1 illustrates a patient draped to expose only an eye for surgery, the drape held away from the face by the drape support of this invention.

Referring to FIG. 1, the surgical drape support 1 uses a supply tube 10 and a suction tube 12 to suspend a surgical drape 14 above a patient's nostrils 16 and mouth 18 while allowing the surgeon unencumbered access to the patient's eye through drape aperture 20.

For manufacturing economy and ease of use, supply tube 10 and suction tube 12 may be made from a single piece of tubing containing a plug 22 to prevent direct communication between the supply 10 and suction 12 portions of the tubing.

One or more (preferably several) supply ports 24 are located at or near the upper end 23 of supply tube 10 for supplying oxygen or air to the patient. Similarly, one or more (preferably several) suction ports 26 are located at or near the upper end 25 of suction tube 12 for removing accumulated $CO_2$-rich exhaled air. The ports may consist simply of holes formed in the tubes 10,12 or may consist of nozzle assemblies.

Also located at the upper ends of the tubes are optional horizontal tabs 42, to which a clamp may be attached to secure the drape and hold it taut. Tabs 42 can also be used to secure other items, such as small containers, to the drape.

Supply tube 10 and suction tube 12 are attached near their lower ends 27, 29 respectively, to bracket 28 on its vertical fin 30. The horizontal base 32 of bracket 28 is disposed beneath a mattress on which the patient is lying. Bracket 28 provides support for surgical drape support 1.

Supply tube 10 at its lower end 33 is coupled to a supply valve 34, which in turn is coupled to an oxygen or air source 36. Likewise, suction tube 12 at its lower end 37 is coupled to a suction valve 38, which is in turn coupled to a suction source 40. The valves are for the convenience of the anesthesiologist and may be omitted in an alternative configuration.

Because the tubes must support the weight of the drape, they must be rigid, but be capable of being shaped. Malleable tubes allow the surgeon to easily manipulate surgical drape support 1 to accommodate variations in patient size and shape. In one embodiment, the tubes are formed from a single piece of soft copper tubing covered by a crosslinked fluoropolymer or polyolefin tubing, or similar material. Plug 22 is formed by blocking the tubing, and ports 24, 26 are made by drilling holes into the tubing on either side of plug 22. In another embodiment, the tubes are formed from a tandem series of commercially available ball and socket tubing links. Special purpose links are available, such as links with nozzles (to form ports 24,26) and valves (to form plug 22).

FIG. 2 illustrates an alternate embodiment of the invention with a loop 50 at or near base 30. Loop 50 allows greater freedom in shaping and positioning drape support 1 over the patient.

While preferred embodiments of the invention have been illustrated in detail, it is apparent that modifications and adaptations of the preferred embodiments will occur to those skilled in the art. It is to be expressly understood that such modifications and adaptations are in the spirit and scope of the invention as set forth in the following claims:

What is claimed is:

1. A surgical apparatus comprising,
a bracket (28) having a horizontal base (32) and a vertical fin (30), said horizontal base designed and arranged for placement beneath a patient bed such that said vertical fin (30) is disposed along side of said patient bed,
a supply tube (10) connected to a source of oxygen (36), said supply tube carried by said bracket and formed of rigid yet malleable material so that said supply tube can be shaped in to a position above a patient lying on said patient bed, said supply tube having a supply port (24) disposed at an upper portion (23) of said supply tube, and
a suction tube (12) connected to a suction source (40), said suction tube carried by said bracket and formed of rigid yet malleable material so that said suction tube can be shaped in to a position above said patient lying on said patient bed, said suction tube having a suction port (26) disposed at an upper portion (25) of said suction tube,
said supply tube (10) and said suction tube (12) being arranged and designed to support a surgical drape (14) above a patient's nostrils (16) and mouth (18).

2. The surgical drape of claim 1 further comprising,
a tab (42) disposed at said upper portion of said supply tube and attached thereto, said tab being arranged and designed to allow securement of said drape or an object with a clamp.

3. The surgical drape of claim 1 further comprising,
a tab (42) disposed at said upper portion of said suction tube and attached thereto, said tab being arranged and designed to allow securement of said drape or an object with a clamp.

4. The surgical drape of claim 1 further comprising,
a supply valve (34) coupled to said lower end (33) of said supply tube (10).

5. The surgical drape of claim 1 further comprising,
a suction valve (38) coupled to said lower end (37) of said suction tube (12).

6. The surgical drape of claim 1 wherein,
said supply tube (10) and said suction tube (12) form a loop (50) near said vertical fin (30) of said bracket (28).

7. The surgical drape of claim 1 wherein,
said upper portion (23) of said supply tube (10) is coupled to said upper portion (25) of said suction tube (12) with no fluid communication therebetween.

8. The surgical drape of claim 7 wherein,
said upper portion (23) of said supply tube (10) and said upper portion (25) of said suction tube (12) are formed into a generally horizontal loop.

9. A method for draping a patient for surgery comprising the steps of,
positioning an oxygen supply tube (10) and a suction tube (12) generally above a patient's lower face, neck and chest, said supply tube (10) having a supply port (24) located near the patient's face, said suction tube (12) having a suction port (26) located near the patient's face,
connecting said supply tube (10) to an oxygen source (36),
connecting said suction tube (12) to a suction source (40), and
supporting a drape (14) with at least on of said supply tube (10) or said suction tube (12) in a position over the patient to prevent said drape (14) from contacting the patient's nostrils (16) and mouth (18).

10. The method of claim 9 further comprising the steps of,
controlling a flow of oxygen through said supply tube (10) by a supply valve (34), and
controlling suction through said suction tube (12) by a suction valve (38).

11. A surgical apparatus comprising,
a bracket (28) having a horizontal base (32) and a vertical fin (30), said horizontal base designed and arranged for placement beneath a patient bed such that said vertical fin (30) is disposed along side of said patient bed,
a supply tube (10) connected to a source of oxygen (36), said supply tube carried by said bracket and formed of rigid yet malleable material so that said supply tube can be shaped in to a position above a patient lying on said patient bed, said supply tube having a supply port (24) disposed at an upper portion (23) of said supply tube, and
a suction tube (12) connected to a suction source (40), said suction tube carried by said supply tube, said suction tube having a suction tube (26) disposed at an upper portion (25) of said suction tube,
said supply tube (10) being arranged and designed to support a surgical drape (14) above a patient's nostrils (16) and mouth (18).

12. The surgical drape of claim 11 further comprising,
a tab (42) disposed at said upper portion of said supply tube and attached thereto, said tab being arranged and designed to allow securement of said drape or an object with a clamp.

13. The surgical drape of claim 11 further comprising,
a supply valve (34) coupled to said lower end (33) of said supply tube (10).

14. The surgical drape of claim 11 further comprising,
a suction valve (38) coupled to said lower end (37) of said suction tube (12).

15. The surgical drape of claim 11 wherein,
said supply tube (10) and said suction tube (12) form a loop (50) near said vertical fin (30) of said bracket (28).

* * * * *

UNITED STATES PATENT AND TRADEMARK OFFICE
CERTIFICATE OF CORRECTION

PATENT NO. : 6,871,651 B2
DATED : March 29, 2005
INVENTOR(S) : Jeffrey Day Lanier It is certified that error appears in the above-identified patent and that said Letters Patent is hereby corrected as shown below:

Column 4,
Line 24, delete the word "on" and insert the word -- one --
Line 46, delete the second occurrence of the word "tube" and insert the word -- port --

Signed and Sealed this

Thirty-first Day of May, 2005

JON W. DUDAS
*Director of the United States Patent and Trademark Office*